US00PP18590P2

(12) United States Plant Patent
Klemm

(10) Patent No.: US PP18,590 P2
(45) Date of Patent: Mar. 11, 2008

(54) ***PETUNIA* PLANT NAMED 'KLEPH05117'**

(50) Latin Name: *Petunia×hybrida*
Varietal Denomination: KLEPH05117

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/524,420

(22) Filed: Sep. 20, 2006

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent Bell
(74) *Attorney, Agent, or Firm*—C. A. Whealy

(57) ABSTRACT

A new and distinct cultivar of *Petunia* plant named 'KLEPH05117', characterized by its outwardly spreading to trailing growth habit; freely branching habit; freely flowering habit; relatively large yellow green-colored flowers; and good garden performance.

1 Drawing Sheet

Botanical designation: *Petunia×hybrida.*
Cultivar denomination: 'KLEPH05117'.

BACKGROUND OF THE INVENTION

The present invention relates to a new and distinct cultivar of *Petunia,* botanically known as *Petunia×hybrida* and hereinafter referred to by the name 'KLEPH05117'.

The new *Petunia* is a product of a planned breeding program conducted by the Inventor in Stuttgart, Germany. The objective of the breeding program is to create new freely-branching *Petunia* cultivars with compact and trailing plant habit, early and freely flowering habit, and unique and attractive flower color.

The new *Petunia* originated from a cross-pollination made by the Inventor during the summer of 2002 in Stuttgart, Germany of a proprietary selection of *Petunia×hybrida* identified as code number J 103, not patented, as the female, or seed, parent with a proprietary selection of *Petunia×hybrida* identified as code number J 138, not patented, as the male, or pollen, parent. The new *Petunia* was discovered and selected by the Inventor as a single flowering plant within the progeny of the stated cross-pollination in a controlled environment in Stuttgart, Germany in May, 2003.

Asexual reproduction of the new *Petunia* by terminal cuttings in a controlled environment in Stuttgart, Germany since June, 2003, has shown that the unique features of this new *Petunia* are stable and reproduced true to type in successive generations.

SUMMARY OF THE INVENTION

The cultivar KLEPH05117 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLEPH05117'. These characteristics in combination distinguish 'KLEPH05117' as a new and distinct cultivar of *Petunia:*

1. Outwardly spreading to trailing growth habit.
2. Freely branching habit.
3. Freely flowering habit.
4. Relatively large yellow green-colored flowers.
5. Good garden performance.

Plants of the new *Petunia* can be compared to plants of the female parent selection. Plants of the new *Petunia* differ primarily from plants of the female parent selection in flower color as plants of the female parent selection have pink and yellow-colored flowers.

Plants of the new *Petunia* can be compared to plants of the male parent selection. Plants of the new *Petunia* differ from plants of the male parent selection in the following characteristics:

1. Plants of the new *Petunia* have larger flowers than plants of the male parent selection.
2. Plants of the new *Petunia* are more tolerant to low temperatures than plants of the male parent selection.

Plants of the new *Petunia* can be compared to plants of the *Petunia* cultivar Famous Yellow, not patented. In side-by-side comparisons conducted in Stuttgart, Germany, plants of the new *Petunia* differed from plants of the cultivar Famous Yellow in the following characteristics:

1. Flower color of plants of the new *Petunia* was more intense than flower color of plants of the cultivar Famous Yellow.
2. Plants of the new *Petunia* were more tolerant to low temperatures than plants of the cultivar Famous Yellow.

BRIEF DESCRIPTION OF THE PHOTOGRAPH

The accompanying colored photograph illustrates the overall appearance of the new *Petunia,* showing the colors as true as it is reasonably possible to obtain in colored reproductions of this type. Colors in the photograph may differ slightly from the color values cited in the detailed botanical description which accurately describe the colors of the new *Petunia.* The photograph comprises a side perspective view of typical flowering plants of 'KLEPH05117' grown in a hanging basket container.

DETAILED BOTANICAL DESCRIPTION

The photograph and following observations, measurements and values describe plants grown in Stuttgart, Germany, under commercial practice during the spring in a glass-covered greenhouse with day temperatures averaging 18° C., night temperatures averaging 14° C. and light levels averaging 20,000 lux. Rooted young plants had been growing for about five months when the photograph and description were taken. Plants used for the description were grown in 12-cm containers. In the following description, color references are made to The Royal Horticultural Society Colour Chart, 1995 Edition, except where general terms of ordinary dictionary significance are used.

Botanical classification: *Petunia×hybrida* cultivar KLEPH05117.

Parentage:

*Female, or seed, parent.*—Proprietary selection of *Petunia×hybrida* identified as code number J 103, not patented.

*Male, or pollen, parent.*—Proprietary selection of *Petunia×hybrida* identified as code number J 138, not patented.

Propagation:

*Type.*—By terminal cuttings.

*Time to produce a rooted young plant, summer.*—About three weeks at temperatures of 20° C. to 26° C.

*Time to produce a rooted young plant, winter.*—About 25 days at temperatures of 20° C.

*Root description.*—Fine, fibrous; white in color.

*Rooting habit.*—Freely branching; moderately dense.

Plant description:

*Plant and growth habit.*—Outwardly spreading to trailing growth habit. Freely branching habit with about seven primary lateral branches each with multiple secondary lateral branches; pinching is typically not required. Moderately vigorous growth habit.

*Plant height.*—About 13 cm.

*Plant diameter.*—About 20 cm.

Lateral branch description:

*Length.*—About 12 cm.

*Diameter.*—About 2.5 mm.

*Internode length.*—About 0.5 cm to 3.5 cm.

*Strength.*—Strong.

*Aspect.*—Initially upright to outwardly spreading.

*Texture.*—Smooth, glabrous.

*Color.*—137C.

Foliage description:

*Arrangement.*—Alternate, simple.

*Length.*—About 2.5 cm to 3 cm.

*Width.*—About 2 cm to 2.5 cm.

*Shape.*—Broadly elliptic.

*Apex.*—Acute.

*Base.*—Obtuse.

*Margin.*—Entire; weakly undulate.

*Texture, upper surface.*—Slightly pubescent.

*Texture, lower surface.*—Smooth, glabrous.

*Venation pattern.*—Pinnate; arcuate.

*Color.*—Developing foliage, upper surface: 143B. Developing foliage, lower surface: 143C. Fully expanded foliage, upper surface: 143A; venation, 144B. Fully expanded foliage, lower surface: 143C; venation, 144C.

*Petiole length.*—About 2 mm to 3 mm.

*Petiole diameter.*—About 3 mm.

*Petiole texture, upper and lower surfaces.*—Smooth, glabrous.

*Petiole color, upper surface.*—143A.

*Petiole color, lower surface.*—143C.

Flower description:

*Flower arrangement and habit.*—Relatively large salverform flowers arranged singly arising from leaf axils. Freely flowering habit with usually about 20 open flowers and flower buds developing per lateral branch. Flowers not persistent. Flowers face mostly upright to outwardly.

*Fragrance.*—None detected.

*Natural flowering season.*—Plants flower continuously throughout the summer in Germany.

*Flower longevity.*—Individual flowers last about one week on the plant.

*Flower diameter.*—About 6 cm.

*Flower length (height).*—About 7 cm.

*Flower throat diameter.*—About 1.5 cm.

*Flower tube diameter.*—About 5 mm.

*Flower tube length.*—About 2.5 cm.

*Flower bud.*—Shape: Elongated oblong. Length: About 3.5 cm. Diameter: About 1.8 cm. Color: 145A.

*Corolla.*—Arrangement: Five petals fused at the base and opening into a flared trumpet. Petal length from throat: About 2.5 cm to 3.5 cm. Petal lobe width: About 2.8 cm. Petal shape: Roughly cordate. Petal apex: Crenate. Petal margin: Entire; undulating. Petal texture, upper and lower surfaces: Smooth, glabrous; satiny. Throat and tube texture: Smooth, glabrous. Color: Petal, when opening and fully opened, upper surface: 150D; central star, 154B; venation, 154B. Petal, when opening and fully opened, lower surface: 150D; venation, 154B. Throat: 3A; venation, 3A. Tube: 3B; venation, 3B.

*Calyx.*—Arrangement: One star-shaped calyx tube with five sepals fused at the base per flower. Sepal length: About 1.5 cm. Sepal width: About 5 mm. Sepal shape: Lanceolate to elliptical. Sepal apex: Obtuse. Sepal margin: Entire. Sepal texture, upper and lower surfaces: Smooth, glabrous. Color, upper surface: 138A. Color, lower surface: 138B.

*Peduncles.*—Length: About 7 cm. Diameter: About 3 mm. Angle: Erect to about 60° from stem axis. Strength: Moderately strong. Texture: Smooth, glabrous. Color: 137C.

*Reproductive organs.*—Stamens: Quantity/arrangement: Four per flower. Anther shape: Elliptic. Anther length: About 3 mm. Anther color: 2C. Pollen amount: Moderate. Pollen color: 2B. Pistils: Quantity: One per flower. Pistil length: About 9 mm. Style length: About 5 mm. Style color: 1C. Stigma shape: Oval. Stigma color: 1C. Ovary color: 1C. Seed/fruit: Seed and fruit development have not been observed on plants of the new *Petunia*.

Garden performance: Plants of the new *Petunia* have been observed to have good garden performance and tolerate wind, rain and temperatures ranging from about 6° C. to about 50° C.

Pathogen/pest resistance: Plants of the new *Petunia* have not been observed to be resistant to pathogens and pests common to *Petunia*.

It is claimed:

1. A new and distinct *Petunia* plant named 'KLEPH05117' as illustrated and described.

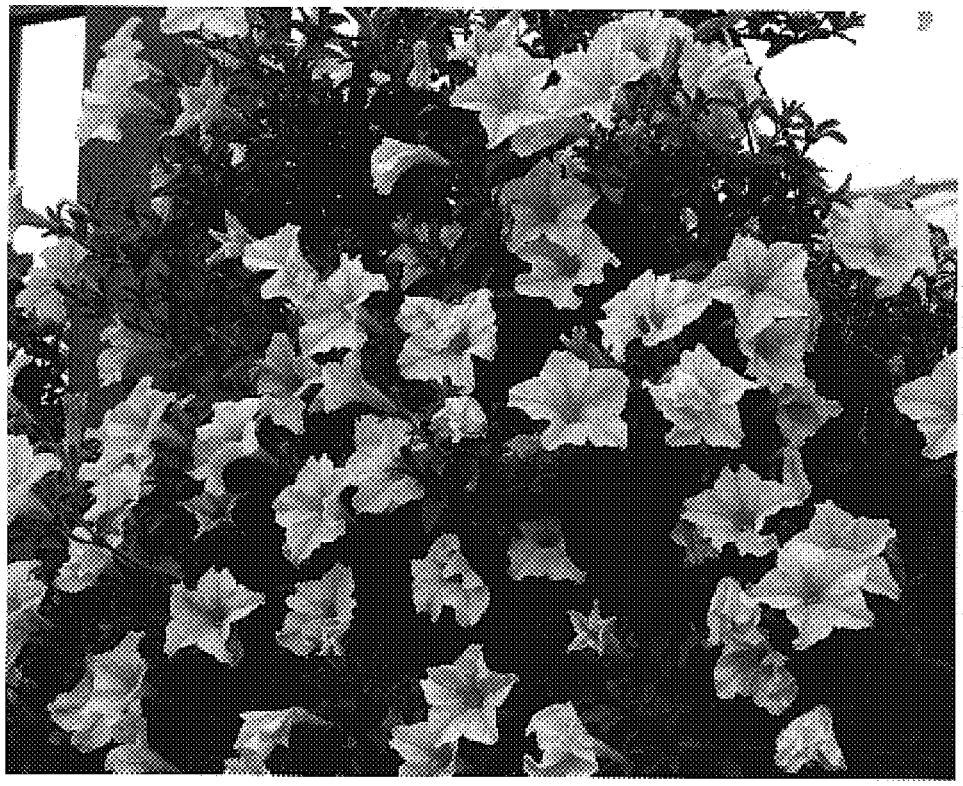

* * * * *